United States Patent [19]

Yamakawa et al.

[11] Patent Number: 5,217,305
[45] Date of Patent: Jun. 8, 1993

[54] METHOD OF EVALUATING CERAMICS

[75] Inventors: Akira Yamakawa; Masaya Miyake, both of Hyogo; Kozo Ishizaki, Niigata; Koji Watari, Aichi, all of Japan

[73] Assignee: Sumitomo Electric Industries, Ltd., Osaka, Japan

[21] Appl. No.: 867,876

[22] Filed: Apr. 13, 1992

[30] Foreign Application Priority Data

Apr. 16, 1991 [JP] Japan .................................. 3-110972

[51] Int. Cl.⁵ ............................................. G01N 25/00
[52] U.S. Cl. ......................................... 374/45; 374/31; 73/866
[58] Field of Search ............... 374/5, 31, 33, 40, 43, 374/45, 53, 55, 57; 73/866, 32 R

[56] References Cited

U.S. PATENT DOCUMENTS

| | | | |
|---|---|---|---|
| 4,154,099 | 5/1979 | Blu et al. | 374/31 |
| 4,210,027 | 7/1980 | Patterson | 73/866 |
| 4,542,345 | 9/1985 | Tomasulo | 374/45 |
| 4,559,824 | 12/1985 | Soma | 374/57 |
| 4,636,969 | 1/1987 | Kyoden | 374/55 |
| 4,762,424 | 8/1988 | Baricevac | 374/55 |
| 4,933,887 | 6/1990 | Dankó et al. | 374/45 |

FOREIGN PATENT DOCUMENTS 0129419 12/1984 European Pat. Off. .
279802 6/1990 Fed. Rep. of Germany .
63-1955 1/1988 Japan .

OTHER PUBLICATIONS

Soviet Inventions Illustrated, Mar. 12, 1986; SU 1,167-479-A; Jul. 15, 1985.

Primary Examiner—William A. Cuchlinski, Jr.
Assistant Examiner—G. Bradley Bennett
Attorney, Agent, or Firm—W. G. Fasse

[57] ABSTRACT

For evaluating mechanical properties of ceramics such as silicon nitride in a nondestructive manner, a specific heat of ceramic test samples to be evaluated is measured at a temperature not higher than room temperature. A comparison is made between a measured value of the specific heat of the test sample and a known value of a specific heat of a ceramic reference sample at the same temperature not higher than room temperature. The comparison, permits making conclusions regarding the mechanical properties of the ceramic test samples based on the known mechanical properties of the ceramic reference sample. The creep strength is given as one example of the mechanical properties that may be ascertained by a nondestructive inspection that may be part of a production line, whereby the mechanical properties of the individual ceramic products may be guaranteed in practice.

6 Claims, 2 Drawing Sheets

METHOD OF EVALUATING CERAMICS

FIELD OF THE INVENTION

The present invention relates to a method of evaluating ceramics and, more particularly, to a method of evaluating properties of ceramics by nondestructive testing, to ascertain, for example, mechanical properties of ceramics such as the creep characteristic.

BACKGROUND INFORMATION

The properties of ceramics change greatly according to its manufacture process. It is thus indispensable to evaluate the properties of each ceramic product after the manufacture of the product. Conventionally, numerous methods for evaluating the properties of ceramics in either a destructive manner or nondestructive manner have been considered. Silicon nitride ($Si_3N_4$) will now be described as one example of ceramics.

Silicon nitride is noted as an industrial ceramic used for making structural members such as automobile engine components, intended to work at high temperatures such as automobile engine components. Since sintering of silicon nitride alone is difficult, however, a sintering aid made of a low-melting point compound is generally added to silicon nitride powder for sintering. Oxides of aluminum, magnesium, yttrium, lanthanum, cerium, beryllium or zirconium are used, for example, alone or in combination as a sintering aid for sintering silicon nitride.

A sintered body of silicon nitride having a higher density can be achieved by use of the sintering aid than without such an aid. However, the sintering aid remains as a glass phase or a crystal phase of lower strength, hereinafter referred to as "glass phase or the like", in a grain boundary of a resultant sintered body. It is thus difficult to obtain a silicon nitride sintered body having the required mechanical property such as a desired strength. However, when the silicon nitride sintered body is manufactured by pressure sintering such as a Hot Press method or an HIP method, it is possible to reduce or eliminate the amount of the sintering aid previously added. Nevertheless, the manufacture of the silicon nitride sintered body by such pressure sintering has the disadvantage that it is difficult to carry out successive sintering steps, resulting in an increase in the manufacturing cost.

Accordingly, at present, a silicon nitride sintered body which is obtained industrially includes a glass phase or the like in its grain boundary. It is considered in general that mechanical properties such as the material strength in ceramics, such as silicon nitride, deteriorate with an increase in the amount of the glass phase or the like included in the ceramics. It is extremely significant to precisely measure the amount of the glass phase or the like included in the ceramics, in order to manufacture ceramics such as silicon nitride having excellent mechanical properties such as material strength. However, a nondestructive inspection which can be introduced into a production line of ceramics so that products travelling along the line can be directly inspected for measuring the amount of glass phase or the like, has been unknown heretofore.

More specifically, conventional methods of measuring the amount of glass phase or the like included in ceramics such as silicon nitride involve the following: A structure observation method permits observing the structure or texture of a sintered body having abraded surfaces by employing a microscope or the like; an X-ray diffraction method for photographing an X-ray diffraction image of a sintered body which is ground to have a predetermined thickness; a method for processing a sintered body in a predetermined shape and measuring an internal friction as disclosed in Japanese Patent Laying-Open No. 63-1955. In accordance with the foregoing conventional methods, it is impossible to measure the amount of glass phase or the like included in ceramics, in a nondestructive manner, and hence, only a sampling inspection can be carried out on the production line. Thus, there has been no practical possibility of guaranteeing the amount of the glass phase or the like in conventionally produced ceramic products.

SUMMARY OF THE INVENTION

It is an object of the present invention to provide a method that can be part of a production line and which is capable of evaluating individual ceramic components by a nondestructive testing.

Another object of the present invention is to provide a method of evaluating mechanical properties of ceramic components by nondestructive testing.

A further object of the present invention is to provide a method of evaluating the creep characteristic of ceramic components by nondestructive testing.

A still further object of the present invention is to provide a method of evaluating the mechanical properties of a silicon nitride sintered body by nondestructive testing.

In accordance with a method of evaluating ceramics according to one aspect of the present invention, the specific heat of a ceramic component test sample to be evaluated, is measured at a predetermined temperature. The measured value of the specific heat of the ceramic test sample and a known specific heat value of a ceramic reference sample at that same predetermined temperature are then compared with each other. By this comparison, mechanical evaluation object ceramic are based on the known mechanical properties of the ceramic reference sample.

In accordance with another aspect of the present invention for evaluating ceramic components the specific heat of each of a plurality of ceramic reference components is measured at a predetermined temperature. Also, the mechanical properties of each of these ceramic reference components are measured. A correlation between the measured specific heats and the measured mechanical properties is determined. Further, a specific heat of a ceramic test sample to be evaluated, is measured at a predetermined temperature. By using the above-described correlation resulting, the mechanical properties of the ceramic test sample are obtained from a measured value of the specific heat of the ceramic reference sample.

In accordance with still another aspect of the present invention for evaluating ceramic components the specific heat of each of a plurality of ceramic reference samples is measured at a predetermined temperature. The amount of glass phase included in each of these ceramic reference samples is also measured. Then, a correlation between the measured specific heats and the measured amount of glass phase is determined. Further, the specific heat of ceramic test samples to be evaluated is measured at a predetermined temperature. By using the above-described correlation, the amount of glass phase included in the ceramic test samples is obtained from a measured value of the specific heat of any ceramic test sample.

The inventors of the present application paid special attention to the fact that the specific heat of a glass phase or the like formed of an oxide of aluminum or, for example, which is to be added as a sintering aid, is high in a low temperature region. Thus, we discovered that by measuring and comparing specific heats of ceramics at temperatures not higher than room temperature, we were able to make a precise comparison in the amounts of glass phase or the like included in the ceramics and to further make a comparison in the mechanical properties of the ceramics. The present invention was made on the basis of such discovery and conclusions made by the inventors.

That is, the specific heat of a substance changes, in general, in accordance with temperature. However, while crystallized ceramics such as silicon nitride has a small specific heat at a low temperature, the glass phase or the like formed of the above-described oxide has a large specific heat in a low temperature region. Thus, the specific heat of ceramics such as a silicon nitride sintered body including a glass phase or the like is in the amount of glass phase or the like included therein, in the low temperature region in which the specific heat of glass phase or the like is larger than that of the crystal phase. In addition, even if there is only a slight change in the amount of the glass phase or the like the specific heat of the corresponding ceramic material is subject to a substantially large change. The low temperature region, in which the above relation between temperature and specific heat is obtained, is a temperature range not higher than room temperature, i.e., a range between room temperature and absolute zero degree. Our invention is based on our discovery of the just described relationship between the temperature, the specific heat, and the amount of the glass phase included in the ceramic material.

Accordingly, if silicon nitride is taken as an example, the specific heat of a certain silicon nitride sintered body is measured at a temperature not higher than room temperature by a normal method by utilizing a normal freezing mixture or a cryostat apparatus (low temperature thermostat) employing liquid nitrogen, liquid helium or the like. Independently of this measured value of the specific heat of a test sample, a reference specific heat value of a reference sample of a silicon nitride sintered body, the amount of a glass phase or the like of which is known by the structure observation method or the like or which has predetermined mechanical properties, is measured at the same temperature as the above temperature not higher than room temperature. By comparing this reference specific heat value with the measured specific heat value of the above-described silicon nitride sintered body test sample, it becomes possible to evaluate or ascertain the relative amount of the glass phase or the like and hence the mechanical properties of the silicon nitride sintered body test sample.

Moreover, the amount of the glass phase or the like and hence the mechanical properties, and specific heats at a temperature not higher than room temperature are measured, respectively, and compared to a large number of silicon nitride sintered bodies providing reference values. By plotting a graph of these reference values the correlation between the measured amount of the glass phase or the like and the measured mechanical properties and the measured specific heats are obtained as correlation curves. On the other hand, the specific heat of the silicon nitride sintered body forming the test sample is measured at the same temperature as above. Thus, it is possible to obtain as absolute values the amount of glass phase or the mechanical properties of that sintered body from a measured value of its specific heat by employing the above-described correlation curves.

The ceramics evaluation method of the present invention is also applicable to various other types of ceramics such as aluminum nitride, silicon carbide, aluminum oxide, zirconium oxide or mullite. In other words, the present method is not limited to silicon nitride.

As described above, according to the ceramics evaluation method of the present invention, there is no need to destroy or process the ceramic test sample that is to be evaluated. Therefore, a sampling inspection is avoided and an inspection of a nondestructive nature performed on the production line is available. This makes it possible to guarantee the amount of glass phase or the like and respective mechanical properties of ceramic components as they are actually produced. Further, the evaluation by the method of the present invention provides information as to all individual ceramics, not partial information limited to a specific part of ceramics as by the X-ray diffraction method.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

EXAMPLE 1

$Si_3N_4$ powder having average grain size of 0.8 μm and 1.5% by weight of oxygen content, $Y_2O_3$ powder, $Al_2O_3$ powder and $SiO_2$ powder were prepared. These powders were mixed together to form such compositions as are shown in Table 1 below, and the respective samples were sintered under respective sintering conditions shown in Table 1. Sample No. 1 consisting of the $Si_3N_4$ powder was, however, subjected to HIP sintering by a glass capsule method.

TABLE 1

| Sample Number | Composition of sintered body | | | | Sintering Condition (°C. × hr) |
|---|---|---|---|---|---|
| | $Si_3N_4$ | $Y_2O_3$ | $Al_2O_3$ | $SiO_2$ | |
| 1 | 100 | — | — | — | 1750 × 2 |
| 2 | 96 | 3 | 1 | — | " |
| 3 | 92 | 5 | 3 | — | " |
| 4 | 87 | 5 | 3 | 5 | " |
| 5 | — | 61 | 28 | 11 | 1600 × 1 |

Each of the resultant sintered bodies was put into a cryostat apparatus, and the respective specific heat was measured in a temperature range of −271° C. to room temperature by using a calorimeter, and specific heats at −268° C. (5K) were obtained. Then, the amount of glass phase or the like included in each sintered body was measured, and a creep strength at 1350° C. ×500 hr and fracture toughness of each sintered body was measured. The result is shown in Table 2 below.

TABLE 2

| Sample Number | Glass phase (mol %) | Specific heat (J/K · Kg) | Creep Strength (MPa) | Fracture toughness (MN/m$^{3/2}$) |
| --- | --- | --- | --- | --- |
| 1 | 0 | 0.1825 | 300 | 4 |
| 2 | 5 | 0.1910 | 250 | 6 |
| 3 | 10 | 0.2050 | 200 | 7 |
| 4 | 20 | 0.2310 | 150 | 6 |
| 5 | 100 | 0.3200 | 10 | 1 |

Figure 1:
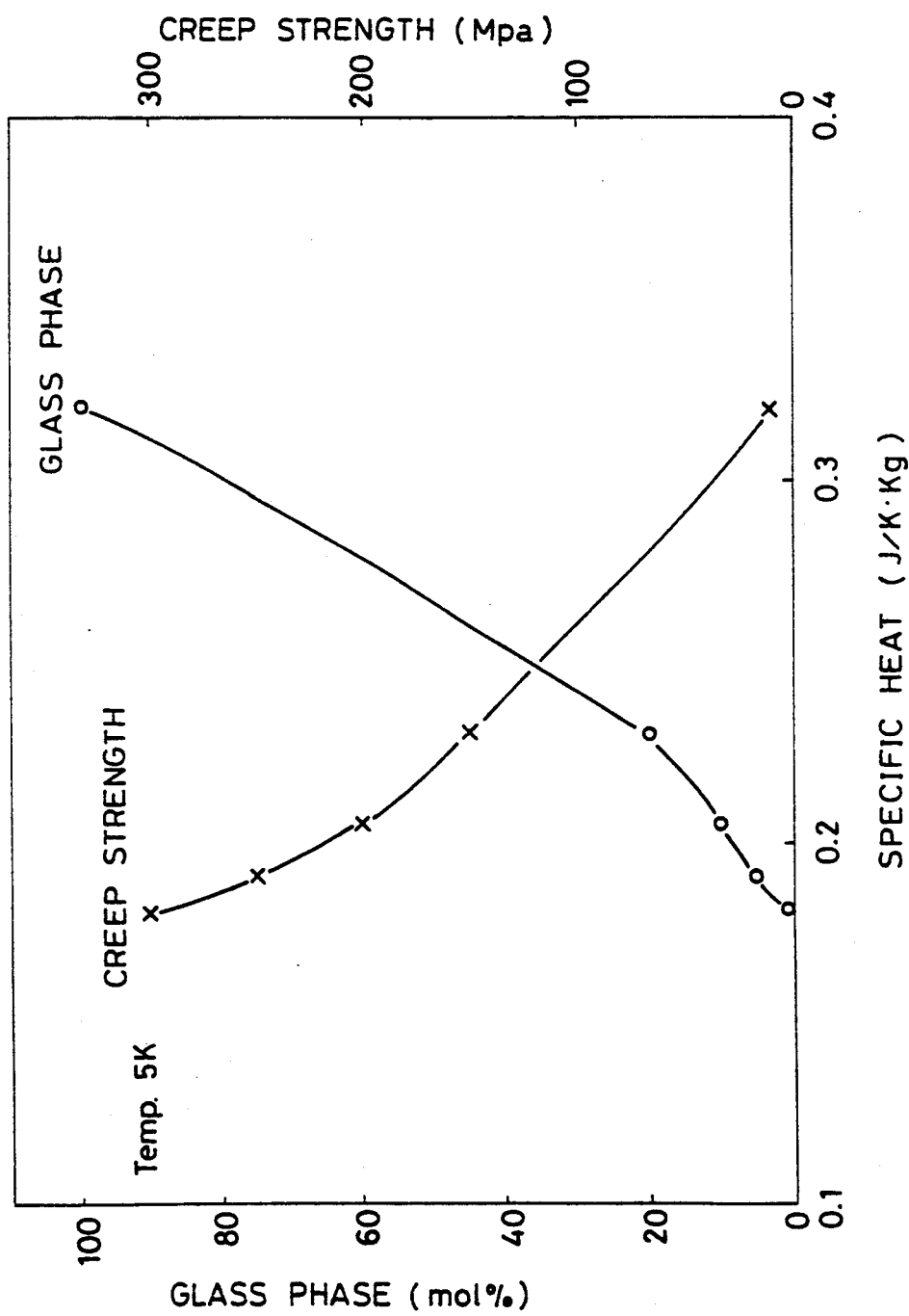
FIG. 1 is a graph showing the relationship between a specific heat and a creep strength and the amount of glass phase of a silicon nitride sintered body provided as reference ceramic sample based on Example 1.

A relationship between the amount of glass phase and the creep strength on the one hand and the specific heat (of each sample), was determined based on Table 2, is shown in FIG. 1. Curves shown in FIG. 1 are indicative of a correlation between the creep strength and the amount of the glass phase content as a function of the specific heat of the ceramic reference samples. As is apparent from FIG. 1, it is understood that a sintered body having a larger specific heat has a larger amount of glass phase or the like included therein and a smaller creep strength. This makes it possible to measure the specific heat of a silicon nitride sintered body test sample and to also relatively compare and evaluate the amount of glass phase or the like and the creep strength as one of the mechanical properties of the test samples from the measured values of the specific heat by employing the correlation curves of FIG. 1.

EXAMPLE 2

Figure 2:
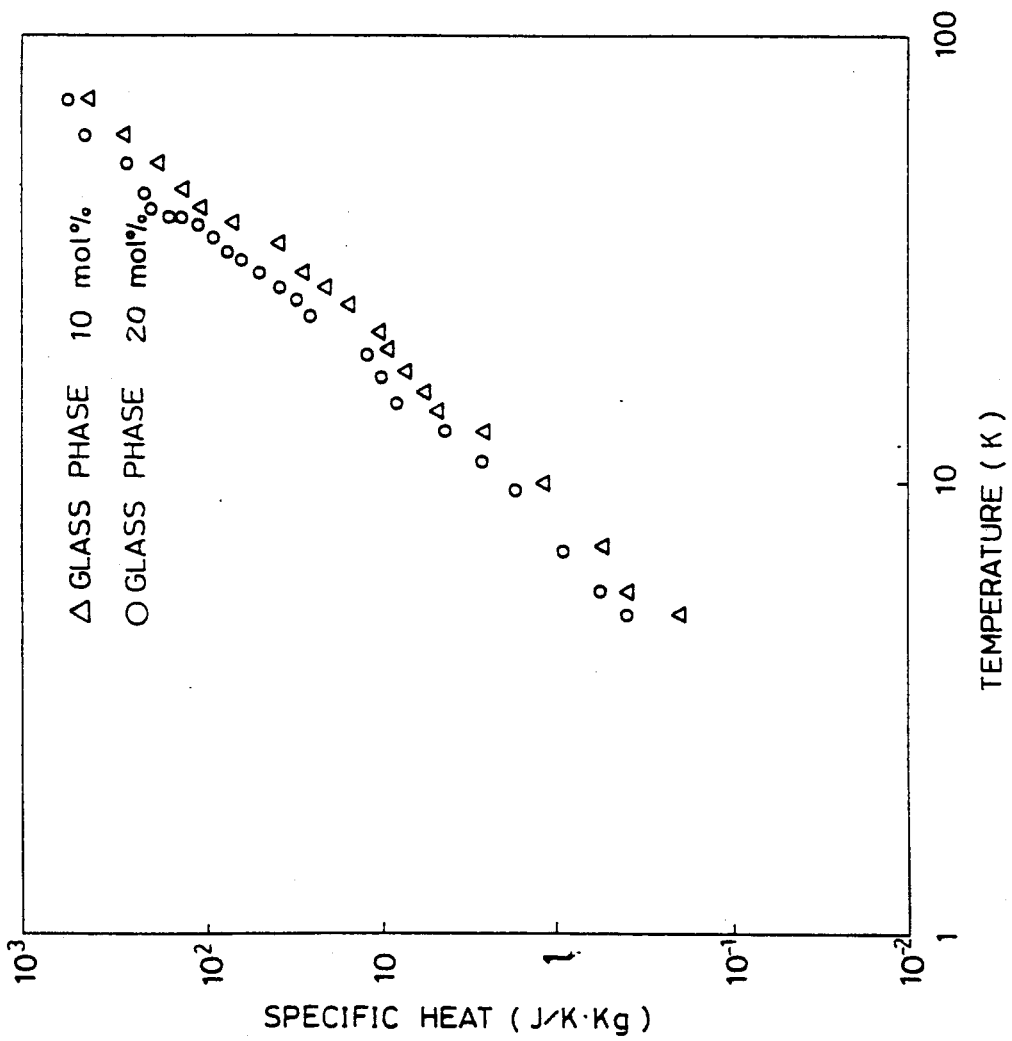
FIG. 2 is a graph showing a relationship between respective specific heats of silicon nitride sintered bodies including different amounts of glass phase in the sintered bodies obtained according to Example 2, and temperatures at which the specific heat was measured.

Y$_2$O$_3$ powder and Al$_2$O$_3$ powder were added to and mixed with Si$_3$N$_4$ powder with an average grain size of 0.5 μm and 2.0% by weight of oxygen content. The mixture was then sintered, and two types of silicon nitride sintered bodies were produced: one type includes 10 mol % of a glass phase, and the other type includes 20 mol % of a glass phase. Respective specific heats of the resultant two sintered bodies were measured in a temperature range of 5K to 76K. The relationships between the specific heats based on the result of measurement and temperature are shown in FIG. 2 which shows that there is a difference in specific heat due to a difference in the amount of glass phase in a low temperature region not higher than room temperature.

As has been described above, according to the present invention, it is possible to evaluate ceramic components such as silicon nitride sintered bodies by a nondestructive inspection used on a production line thereby to guarantee the amount of glass phase and the like or mechanical properties with respect to individual ceramic test samples which are produced on that production line.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A method for evaluating ceramic test samples to be evaluated in a non-destructive manner to ascertain mechanical properties of said ceramic test samples, comprising the following steps: measuring, at a predetermined temperature a specific heat of said ceramic test samples; comparing a measured specific heat value of said ceramic test samples with a known specific heat value of ceramic reference samples having known mechanical properties, said known specific heat value also having been measured at said predetermined temperature, whereby identical specific heat values for said ceramic test samples and for said ceramic reference samples, signify that said ceramic test samples have the same mechanical properties as said known mechanical properties of said ceramic reference samples; and ascertaining from said comparing mechanical properties of said ceramic test samples based on said known mechanical properties of said ceramic reference samples.

2. A method for evaluating ceramic test samples to be evaluated in a non-destructive manner to ascertain mechanical properties of said ceramic test samples, comprising the following steps: measuring a specific heat value of each of a plurality of ceramic reference samples at a predetermined temperature to obtain a corresponding plurality of first specific heat values; measuring mechanical properties of each of said plurality of ceramic reference samples; establishing a correlation between said first specific heat values and said mechanical properties of said ceramic reference samples; measuring a specific heat value of at least one ceramic test sample to be evaluated at said predetermined temperature to obtain a second specific heat value; and ascertaining mechanical properties of said at least one ceramic test sample from said measured second specific heat value of said at least one ceramic test sample by using said correlation.

3. The method according to claim 2, comprising using as said ceramic test sample and as said ceramic reference sample silicon nitride sintered bodies.

4. The method according to claim 2, wherein said predetermined temperature is room temperature at the most.

5. The method according to claim 2, wherein said mechanical properties comprise a creep strength.

6. A method for evaluating ceramic test samples to be evaluated in a non-destructive manner to ascertain mechanical properties of said ceramic test samples, comprising the steps of: measuring a specific heat value of each of a plurality of ceramic reference samples at a predetermined temperature to obtain a corresponding plurality of first specific heat values; measuring an amount of glass phase included in each of said plurality of ceramic reference samples; establishing a correlation between said first specific heat values and said amount of glass phase in said ceramic reference samples; measuring a specific heat value of at least one ceramic test sample to be evaluated at said predetermined temperature to obtain a second specific heat value; and ascertaining an amount of glass phase included in said at least one ceramic test sample from said measured second specific heat value of said at least one ceramic test sample by using said correlation.

* * * * *